(12) United States Patent
Graves et al.

(10) Patent No.: US 6,206,819 B1
(45) Date of Patent: Mar. 27, 2001

(54) HALOGENATION CATALYST

(75) Inventors: Deborah Diane Graves, Bluebell; Thomas Duncan Rose, Levittown; David James Swank, Holland; Charles Chao Wu, North Wales, all of PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 09/572,489

(22) Filed: May 15, 2000

Related U.S. Application Data

(63) Continuation of application No. 08/816,610, filed on Mar. 13, 1997, now abandoned.
(60) Provisional application No. 60/013,500, filed on Mar. 15, 1996.

(51) Int. Cl.[7] .................................................. C07C 63/00
(52) U.S. Cl. .................... 582/855; 562/840; 562/862; 546/315; 570/258; 570/261
(58) Field of Search .................................. 562/840, 855, 562/862; 546/315; 570/258, 261

(56) References Cited

U.S. PATENT DOCUMENTS

| | | |
|---|---|---|
| 3,501,405 | 3/1970 | Willette . |
| 4,129,595 | 12/1978 | Suzuki . |
| 4,777,283 | 10/1988 | Krebs et al. . |
| 4,789,493 | 12/1988 | Horodysky . |
| 4,880,576 | 11/1989 | Blank et al. . |

FOREIGN PATENT DOCUMENTS

| | | |
|---|---|---|
| 0 027 941 | 10/1982 | (DE) . |
| 300 441 | 6/1992 | (DE) . |
| 1106545 | 5/1986 | (JP) . |
| 05140060 | 6/1993 | (JP) . |
| 313468 | 12/1993 | (JP) . |
| 06321877 | 11/1994 | (JP) . |

OTHER PUBLICATIONS

European Search Report, Search Date Jun. 12, 1997.
University of Pennsylvania, Dept. of Chemistry, Aminolysis of Esters of Negatively Substituted Acetic Acids, Dec. 1956, Joullié, Násfay, Rypstat.
J. Med. Chem. (1995) 38, 2830–2841, Synthesis, Structure, and Pharmacological Evaluation of the Stereoisomers of Furnidipine.
Tetrahedron, 1963, vol. 19, pp. 879 to 889. Pergamon Press Ltd., Northern Ireland, Effect of Neighboring Fluorine Atoms on the Spectral Properties of B–Ketoesters, Their Enol Acetates, and Copper Chelates, Illinois Institute of Technology, Dept. of Chemistry, Chicago, R. Filler and S. M. Naqvi.
The Hebrew University, Jerusalem, The Chemistry of Enamines, 1994, edited by Zvi Rappoport, 50309.
Reductive Removal of Sulfonyl Groups: Cleavage of Sulfonamides and Sulfonates by Alkali Metal combined with Crown Ether by T. Ohsawa, T. Takagaki, F. Ikehara, Y. Takahashi, T. Oishi, The Institute of Physical and Chemical Research (RIKEN), Japan, March 1982.
Novel 6–(Trifluoromethyl)cytosines and 6–(Trifluoromethyl) uracils by A. Lutz and S. Trotto, Chemical Research and Development Laboratories, Agricultural Division, American Cyanamid Company, Princeton, NJ 08540. Sep. 28, 1971.
Chemical Abstracts, vol. 73, No. 13, Sep. 28, 1970.

*Primary Examiner*—Alan Siegel
(74) *Attorney, Agent, or Firm*—Thomas D. Rogerson

(57) ABSTRACT

N,N-disubstituted formamides, wherein the substituents are selected to provide formamides which have low volatility, are useful as halogenation catalysts. Such catalysts are generally less hazardous to use than typical formamide halogenation catalysts because toxic catalyst by-products are also less volatile. Methods for using such catalysts are provided.

6 Claims, No Drawings

HALOGENATION CATALYST

This application is a Continuation of application Ser. No. 08/816,610, filed Mar. 13, 1997 now abandoned which was a continuation of Provisional Application Ser. No. 60/013, 500 filed Mar. 13, 1996.

The present invention relates to N,N-disubstituted formamides as halogenation catalysts and use of those catalysts for transforming organic hydroxyl and thiol groups to organohalides.

Many reactions for the conversion of organic hydroxyl and thiol groups to organohalides (for example, the preparation of carboxylic acid chlorides from carboxylic acids) are enhanced by the presence of N-alkylated formamides. Often such reactions require the presence of such catalysts. N,N-dimethyl formamide is one of the most commonly used. Unfortunately, under standard halogenation conditions, the use of N,N-di-loweralkyl formamides results in the formation of N,N-di-loweralkylcarbamoyl halides, which have been found to be animal carcinogens. Such halides are particularly hazardous due to their high volatility. U.S. Pat. No. 4,880,576 discloses N,N-dialkylformamides as chlorination catalysts wherein one alkyl group is a $C_1$–$C_4$ alkyl group, with methyl the preferred group, and the other alkyl group contains at least nine carbon atoms. Use of such catalysts avoids the formation of highly volatile N,N-dialkylcarbamoyl chlorides. However, one limitation in the utility of such catalysts is obtaining the appropriate secondary amine wherein one alkyl group is small, methyl preferred, and the other is large, greater than nine carbons. Furthermore, although volatility is reduced, it is not eliminated so there is still risk to workers and to the environment through exposure to any N,N-dialkylcarbamoyl halide which may be formed.

We have discovered that it is not necessary to limit one, or both, of the alkyl groups of the formamide to less than four carbons in order to maintain halogenation catalyst activity. When the alkyl groups are both large, any N,N-dialkylcarbamoyl halide which may be formed during the halogenation reaction will have very low volatility resulting in less risk to workers and to the environment.

The present invention is the use as a halogenation catalyst of a compound, or mixture of compounds, of formula I:

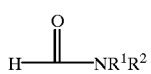

I wherein $R^1$ and $R^2$ are independently selected from:
a. unsubstituted or substituted $C_5$–$C_{30}$ alkyl, $C_5$–$C_{30}$ alkenyl, $C_5$–$C_{30}$ alkynyl, and joined groups; and
b. unsubstituted or substituted amino and polyaminoalkyl and amino and polyaminoalkenyl;
wherein the substituents are independently selected from any functional group which does not react with the substrate to be halogenated or the halogenation agent to be used. Examples of such substituents include alkyl, aryl, halogen, alkoxy, cyano, nitro, formyl and haloalkyl.

A second embodiment of this invention is the use as a halogenation catalyst of a compound, or mixture of compounds, of formula I:

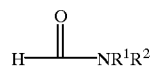

I wherein one of $R^1$ and $R^2$ is independently selected from:
a. unsubstituted or substituted $C_1$–$C_{30}$ alkyl, $C_2$–$C_{30}$ alkenyl, $C_2$–$C_{30}$ alkynyl, and joined groups; and
b. unsubstituted or substituted amino and polyaminoalkyl and amino and polyaminoalkenyl;
wherein the substituents are independently selected from any functional group which does not react with the substrate to be halogenated or the halogenation agent to be used;
and the other of $R^1$ and $R^2$ is a polymer.

The terms "alkyl", "alkenyl", and "alkynyl" include straight chain, branched chain, and cyclic groups. The term "aryl" means phenyl, naphthyl, and five and six membered aromatic heterocycle. The term "joined" means that the $R^1$ and $R^2$ groups together with the nitrogen to which they are attached form a cyclic group such as piperidine and 1,3-di-4-piperidylpropane. The terms "polyaminoalkyl" and "polyaminoalkenyl" mean an alkyl or alkenyl substituted with one or more amino groups. Such amino groups may be primary, secondary, or cyclic amino groups. The amino groups may be of different types within the same polyaminoalkyl or polyaminoalkenyl. Examples of such groups include diaminoalkyls of the formula $R^1N(CHO)$-alkyl-N$(CHO)R^2$, wherein $R^1$ and $R^2$ are as defined above, triaminoalkyls such as bis-(3-aminopropyl)amine, and polyaminoalkyls containing cyclic amine groups. The term "polymer" means any polymer functionalized with one or more amino groups in which the amino group is capable of forming a formamide and the resulting formamide functionalized polymer will not react under the anticipated halogenation reaction conditions. Examples of such polymers include weak base styrenic and acrylic anion exchange resins. Preferred polymers include functionalized ion exchange resins.

Alkyl groups are preferred $R^1$ and $R^2$ groups. Alkyl groups wherein the groups contain more than ten carbon atoms are more preferred because the resulting halogenated product is easily separated from the catalyst. Because of their low cost and high molecular weight, catalysts formed using mixed amines wherein the alkyl groups contain from twelve to twenty-four carbons, such as amines derived from natural fats, are most preferred.

Another embodiment of this invention is a method for converting a substrate to an organohalide, comprising the steps of:
a. forming a mixture comprising the substrate, a halogenating agent, and one or more catalysts of the formula:

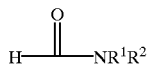

wherein $R^1$ and $R^2$ are independently selected from:
i. unsubstituted or substituted $C_5$–$C_{30}$ alkyl, $C_5$–$C_{30}$ alkenyl, $C_5$–$C_{30}$ alkynyl, and joined groups; and
ii. unsubstituted or substituted amino and polyaminoalkyl and amino and polyaminoalkenyl;
wherein the substituents are independently selected from any functional group which does not react with the substrate to be halogenated or the halogenating agent; and b. maintaining the mixture at a temperature wherein formation of the organohalide occurs at an acceptable rate.

An alternative embodiment of this invention is a method for converting a substrate to an organohalide, comprising the steps of:

a. forming a mixture comprising the substrate, a halogenating agent, and one or more catalysts of the formula:

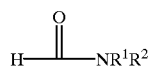

wherein one of $R^1$ and $R^2$ is independently selected from:
i. unsubstituted or substituted $C_1$–C30 alkyl, $C_2$–$C_{30}$ alkenyl, $C_2$–$C_{30}$ alkynyl, and joined groups; and
ii. unsubstituted or substituted amino and polyaminoalkyl and amino and polyaminoalkenyl;
wherein the substituents are independently selected from any functional group which does not react with the substrate to be halogenated or the halogenating agent;
and the other of $R^1$ and $R^2$ is a polymer; and
b. maintaining the mixture at a temperature wherein formation of the organohalide occurs at an acceptable rate.

The term "substrate" means an organic compound containing one or more hydroxyl or thiol groups known to those skilled in the art to be capable of replacement by a halogen using typical halogenation agents. Examples of such substrates include carboxylic acids such as benzoic acid, hexanoic acid, trichloroacetic acid, and succinic acid; N-heterocyclic compounds which carry a hydroxyl group adjacent to the nitrogen, or their tautomeric forms, such as 2-hydroxypyridine, 2,6-dihydroxy4-phenyl-1,3,5-triazine, and 8-hydroxyquinoline; phenols such as picric acid; heterocyclic thiols such as thiazole-2-thiol; and sulfonic acids. The mixture may be formed by combining the components at the same time or by gradually adding one or more of the components. The preferred method of forming the mixture is to gradually add the halogenation agent to a premix of the remaining components. In such cases, the temperature of the premix may be at, above, or below the temperature of step b.

The halogenation reaction may also be used for other types of conversions such as benzaldehyde to benzal chloride, certain dehydration reactions, halogenation of nucleosides and nucleotide coupling, preparation of alkyl halides from alcohols, and the conversion of secondary amides to iminochlorides. The catalyst of this invention is particularly useful for halogenating substrates such as trichloroacetic, terephthalic, and pyridine dicarboxylic acids which are difficult to halogenate in the absence of a catalyst.

The method may be conducted in the absence or presence of a solvent. When a solvent is used it should be reasonably inert to the reaction conditions. Preferred solvents include aromatic and non-aromatic hydrocarbons such as cyclohexane, toluene, and xylenes; ethers and polyethers such as diethyl ether, di-n-butyl ether, and diglyme; esters such as ethyl and n-butyl acetate; and haloalkyls and haloaryls such as methylene chloride, dichloroethane, and chlorobenzene.

The halogenation agent may be one or more of those agents typically used for the halogenation of organic hydroxyl groups. Preferred agents include thionyl chloride, sulfuryl chloride, phosphorous trichloride, phosphorous pentachloride, phosphorous oxychloride, phosgene, oxalyl chloride, and phosgene substitutes such as di- or triphosgene, triphenylphosphine-chlorine complex, and their corresponding bromo analogs.

The temperatures at which the mixture is formed and maintained are not critical. The same or different temperatures may be chosen for each step in the method. The temperatures should be chosen to ensure that the reaction proceeds at an acceptable, controlled rate. Factors to consider in choosing the temperatures include the melting and boiling points of the components of the mixture and the stability of the reactants and the products, particularly the halogenation agent itself.

The organohalide may be separated from the reaction mixture using common separation techniques. The preferred method for organohalides which are sufficiently volatile is to separate them from the catalyst via a distillation process. This allows the residual catalyst to be reused by simply recharging the reaction vessel with additional substrate, halogenating agent, and, when used, solvent. Thus, the method may be conducted either batch-wise or continuously. Other reasonable methods of separation may also be employed, such as precipitation of the catalyst by cooling and then separating it from the organohalide solution using filtration, crystallization of the organohalide (or any subsequent product produced through subsequent reactions) and removing the catalyst in solution in a mother liquor, or, in the case of a polymer based catalyst, using a simple physical separation. Alternatively, the organohalide mixture may be utilized in subsequent reactions without isolation of the organohalide.

Any amount of catalyst may be used depending upon the desired rate of reaction. The greater the usage of catalyst, the faster the halogenation will proceed. It is preferred that the catalyst usage be kept in a ratio of from 0.01 to 100 mole percent of the substrate to balance the benefit of increased rate of reaction against the cost of the catalyst. More preferred is a usage from 0.5 to 5 mole percent. One advantage of the catalysts of this invention is that they are relatively non-volatile. As a result, when the organohalide is separated from the reaction mixture by distillation, the catalyst remains behind and can be reused. In addition, any resulting carbamoyl halide which may be formed as a by-product in the halogenation is similarly non-volatile and, therefore, less hazardous.

The catalyst may be prepared using a general process comprising the steps of: (a) forming a mixture comprising an amine of the formula $HNR^1R^2$, wherein $R^1$ and $R^2$ are as defined above, one or more equivalents of formamide, and one or more equivalents of an acid; (b) heating the mixture to a temperature at or below its boiling point to form the catalyst; and (c) separating the catalyst from the mixture.

Although the amount of formamide used in this reaction is not critical, at least one equivalent is required. We have found that using up to twenty equivalents does not adversely affect the reaction. Cosolvents which do not interfere with the reaction may also be used. Also, the amount of acid is not critical so long as at least one equivalent is used. Use of one to three equivalents of acid is preferred; most preferred is to use only a slight excess, that is, about 1.1 equivalents. Strong, protic acids are preferred. Sulfuric acid is most preferred because it is water soluble and non-volatile. Other acids such as phosphoric acid, polyphosphoric acid, formic acid, and hydrochloric acid are also acceptable.

In those cases wherein the R groups contain twelve to twenty-four carbons, the catalyst product often will solidify when the mixture is cooled. Under these circumstances the catalyst is then easily separated from the mixture. Often, particularly at elevated temperatures, the catalyst may separate from the mixture as an immiscible liquid which is easily isolated.

The following examples describe in detail some of the embodiments of this invention.

EXAMPLE 1

Preparation of Dioctylformamide (DOF)

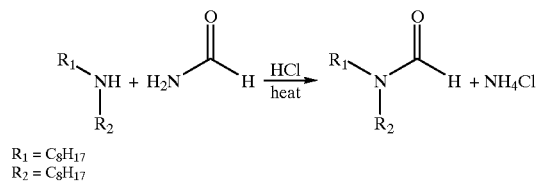

$R_1 = C_8H_{17}$
$R_2 = C_8H_{17}$

| Reagent | MW | Amount | Moles | Eq. |
|---|---|---|---|---|
| Dioctylamine | 241 | 5.0 g | 0.021 | 1 |
| Formamide | 45 | 2.5 g | 0.056 | 2.7 |
| 37% Hydrochloric acid | 36.5 | 6.1 g | 0.062 | 2.9 |
| Cumene | | 40 g | | |

To a 100 mL, 3-necked flask, equipped with a thermometer, a magnetic stirrer, and a condenser atop a Dean-Stark Trap, were added the dioctylamine, hydrochloric acid, and cumene. The mixture was heated to reflux (~150° C.) to remove water.

After all water was removed (~1 h), the mixture was cooled to 120° C. and 2.5 g of formamide was added. The resulting mixture was stirred at 120° C. overnight. The reaction went to completion during this period, as determined by GC analysis.

The mixture was cooled to ambient temperature and washed with water (3×40 mL). The top, product layer was then concentrated in vacuo at 70° C. Upon cooling, a light yellow oil was obtained (5.3 grams, 95% yield). Its identity was confirmed by NMR and GCMS as dioctylformamide.

EXAMPLE 2

Preparation of Di(hydrogenated tallow)formamide (DTF)

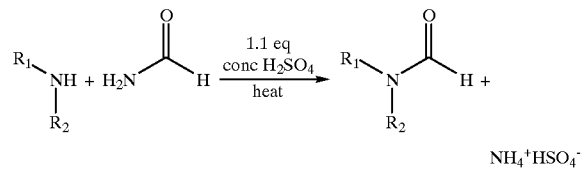

$R_1 = C_{16}H_{33}, C_{18}H_{37}$
$R_2 = C_{16}H_{33}, C_{18}H_{37}$, plus lesser amounts of H, $C_{14}H_{29}$, $C_{15}H_{31}$, $C_{17}H_{35}$

| Reagent | MW | Amount | Moles | Eq. |
|---|---|---|---|---|
| Di(hydrogenated tallow)amine | 480.5* | 50.1 g | 0.104 | 1 |
| Formamide | 45 | 50.5 g | 1.12 | 10.8 |
| Conc. H2SO4 | 98 | 11.8 g | 0.116 | 1.12 |
| Water (each wash) | | 80 g | | |

*Calculated molecular weight based on expected composition

Di(hydrogenated tallow)amine and formamide were added to a 500-mL round bottom flask with bottom take-off, overhead stirrer and nitrogen inertion. The flask was heated using a heating mantle with stirring until the reaction mixture reached a temperature of 85° C. The di(hydrogenated tallow)amine was melted at this temperature. The sulfuric acid was added and then the mixture was heated to 115° C. The reaction was monitored by gas chromatography. Between 2 and 4.5 hours after the mixture reached 115° C. conversion was complete, as judged by disappearance of 2 of the 3 large amine gas chromatographic peaks (in our analysis, a third large peak co-eluted with one of the product peaks).

The mixture was cooled to below 100° C. and 80 g of cold water was added. The mixture was then heated to 90° C., and the lower, aqueous layer was removed. Two more 80 g water washes were conducted at 90° C. The top, product layer was drained to a crystallizing dish and dried in vacuo at 70° C. (as a melt). Upon cooling to room temperature, the product (51.9 grams, 98% yield) was a waxy, light brown solid (mp. 44–46° C.).

EXAMPLE 3

Preparation of a pyridine diacid chloride using DOF

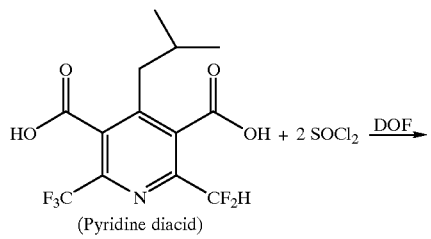

(Pyridine diacid)

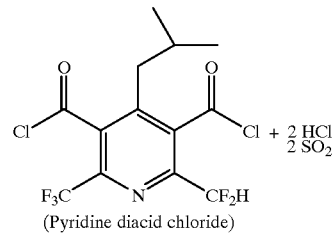

(Pyridine diacid chloride)

| Reagent | MW | Amount | Moles | Eq. |
|---|---|---|---|---|
| Pyridine diacid | 341.2 | 50.0 g | 0.146 | 1 |
| n-Butyl ether | 130.0 | 50.0 g | | |
| Dioctylformamide | 269.0 | 2.0 g | 0.0074 | 0.05 |
| Thionyl chloride | 119.0 | 52.1 g | 0.438 | 3.0 |

Pyridine diacid, n-butyl ether (reaction solvent), and dioctylformamide were added to a 250 ml flask equipped with a magnetic stirrer, reflux/distillation head, nitrogen inertion, and a caustic scrubber. With ice water on the condenser, the flask was heated using a heating mantle to 95° C. Using a syringe pump, the thionyl chloride was added over 3 hours to the reaction mix. The reaction was judged completed based on online FTIR analysis when the thionyl chloride addition was finished.

Excess thionyl chloride and then the n-butyl ether were removed under vacuum to final conditions of 100° C. temperature and 15 mm Hg pressure. Then the pressure was reduced to 1–2 mm Hg and the temperature raised to 130° C. to distill the pyridine diacid chloride. A total of 47.8 g of product was obtained (86.2% yield).

EXAMPLE 4

Preparation of a pyridine diacid chloride using DTF

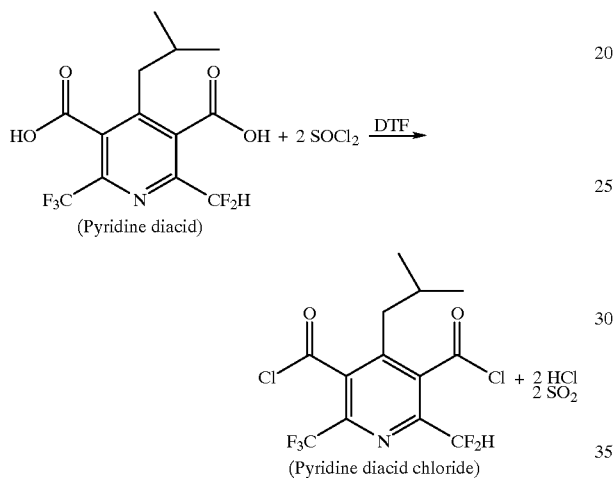

(Pyridine diacid)

(Pyridine diacid chloride)

| Reagent | MW | Amount | Moles | Eq. |
|---|---|---|---|---|
| Pyridine diacid | 341.2 | 58.4 g | 0.171 | 1 |
| n-Butyl acetate | | 61.4 g | | |
| Di(hydrogenated tallow)-formamide (DTF) | 508.0* | 1.75 g | 0.0034 | 0.020 |
| Thionyl chloride | 119.0 | 46.5 g | 0.391 | 2.28 |

*Calculated average molecular weight based on expected composition

Pyridine diacid, n-butyl acetate (reaction solvent), and di(hydrogenated tallow)formamide were added to a 200 ml flask equipped with a magnetic stirrer, reflux/distillation head, nitrogen inertion, and a caustic scrubber. With ice water on the condenser, the flask was heated using a hot oil bath with stirring. Although the di(hydrogenated tallow) formamide was not dissolved at room temperature, the flask contents became homogeneous upon heating to 90° C. Using a syringe pump, the thionyl chloride was added over 3 hours to the reaction mix. The mixture was stirred at 90° C. for an additional 2.5 hours.

Excess thionyl chloride and then the n-butyl acetate solvent were removed under vacuum to final conditions of 100° C. temperature and 15 mm Hg pressure. Then the pressure was reduced to 1–2 mm Hg to evaporate the pyridine diacid chloride overhead. After a forerun cut of 2.7 grams was removed, the flask temperature was increased to 130° C. resulting in 56.9 grams of diacid chloride distillate (91% crude yield after adjusting for samples). Treating the flask with n-butyl acetate solvent and dilute aqueous sodium hydroxide then effectively removed the pot residue and decomposed any carbamoyl chlorides which may have formed.

We claim:

1. A method for converting a substrate to an organohalide, comprising the steps of:
   a. forming a mixture comprising the substrate, a halogenating agent, and one or more catalysts of the formula:

$$H-\overset{O}{\underset{\|}{C}}-NR^1R^2$$

wherein $R^1$ and $R^2$ are independently selected from
   i. unsubstituted or substituted $C_{12}$–$C_{30}$ alkyl, $C_{12}$–$C_{30}$ alkenyl, $C_{12}$–$C_{30}$ alkynyl, and joined groups; and
   ii. unsubstituted or substituted aminoalkyl and polyaminoalkyl and aminoalkenyl and polyaminoalkenyl wherein two or more of the amino groups are in the form of formamides;
   wherein the substituents are independently selected from any functional group which does not react with the substrate to be halogenated or the halogenating agent; and
   wherein the substrate is selected from the group consisting of carboxylic acids, aldehydes, amides, alcohols, N-heterocyclic compounds, phenols, heterocyclic thiols, and sulfonic acids; and
   wherein the halogenating agent is independently selected from the group consisting of thionyl chloride, sulfuryl chloride, phosphorous trichloride, phosphorous pentachloride, phosphorous oxychloride, phosgene, oxalyl chloride, and phosgene substitutes such as do- or tri-phosgene, triphenylphosphine-chlorine complex, and their corresponding bromo analogs; and
   b. maintaining the mixture at a temperature wherein formation of the organohalide occurs at an acceptable rate.

2. A method for converting a substrate to an organohalide, comprising the steps of:
   a. forming a mixture comprising the substrate, a halogenating agent, and one or more catalysts of the formula:

$$H-\overset{O}{\underset{\|}{C}}-NR^1R^2$$

wherein one of $R^1$ and $R^2$ is independently selected from:
   i. unsubstituted or substituted $C_{12}$–$C_{30}$ alkyl, $C_{12}$–$C_{30}$ alkenyl, $C_{12}$–$C_{30}$ alkynyl, and joined groups; and
   ii. unsubstituted or substituted aminoalkyl and polyaminoalkyl and aminoalkenyl and polyaminoalkenyl wherein two or more of the amino groups are in the form of formamides;
   wherein the substituents are independently selected from any functional group which does not react with the substrate to be halogenated or the halogenating agent; and wherein the substrate is selected from the group consisting of carboxylic acids, aldehydes, amides, alcohols, N-heterocyclic compounds, phenols, heterocyclic thiols, and sulfonic acids; and wherein the halogenating agent is independently selected from the group consisting of thionyl chloride, sulfuryl chloride, phosphorous trichloride, phosphorous pentachloride, phosphorous oxychloride, phosgene, oxalyl chloride, and phosgene substitutes such as do- or tri-phosgene, triphenylphosphine-chlorine complex, and their corresponding bromo analogs;

and the other of $R^1$ and $R^2$ is a polymer; and b. maintaining the mixture at a temperature wherein formation of the organohalide occurs at an acceptable rate.

3. The method of claim 1 wherein the mixture further comprises one or more solvents.

4. The method of claim 2 wherein the mixture further comprises one or more solvents.

5. The method of claim 1 wherein the catalyst is reused.

6. The method of claim 2 wherein the catalyst is reused.

* * * * *